United States Patent [19]

Hirashima

[11] Patent Number: 5,160,981
[45] Date of Patent: Nov. 3, 1992

[54] METHOD OF MEASURING THE REFLECTION DENSITY OF AN IMAGE

[75] Inventor: Takuya Hirashima, Kanagawa, Japan
[73] Assignee: Fuji Photo Film Co., Ltd., Kanagawa, Japan
[21] Appl. No.: 573,766
[22] Filed: Aug. 28, 1990
[30] Foreign Application Priority Data Sep. 7, 1989 [JP] Japan .................. 1-232026

[51] Int. Cl.$^5$ .............. G01N 21/47; G01N 21/55
[52] U.S. Cl. ........................ 356/446; 356/448
[58] Field of Search ............. 356/448, 404, 72, 446

Primary Examiner—F. L. Evans
Assistant Examiner—K. P. Hantis
Attorney, Agent, or Firm—Sughrue, Mion, Zinn, Macpeak & Seas

[57] ABSTRACT

A method of measuring a reflected density of visible light from an image recorded on an image recording material. Reflected components of visible and invisible light are measured when a light source is directed at a calibration plate. The calibration plate is then removed and the image recording material is fixed in the position previously occupied by the calibration plate. The same light source is directed at the image recording material and reflected components of invisible and visible light are once again measured. The measured quantity of reflected invisible light reflected from the plate and image recording material respectively are utilized to calculate an error in a measured image density due to spectral absorption. In addition, corrections to a determined image density to compensate for errors due to the angle between the incident light radiated from the lights and a light reflected from the planar image, as well as the angle between the reflected light made incident upon the sensors and a normal to the surface of the sensors are calculated based upon the four different measured reflected components of light.

11 Claims, 5 Drawing Sheets

METHOD OF MEASURING THE REFLECTION DENSITY OF AN IMAGE

BACKGROUND OF THE INVENTION

1. Field of the Invention

The present invention relates to a method of measuring the density of a visible region of a beam of light reflected from a planar image.

2. Description of the Related Art

Conventionally, in order to detect the density at a predetermined position (hereinafter referred to as the detection position) of a planar image recorded on a recording material, a beam of light is radiated from above the detection position, and the quantity of the light beam reflected from the image is detected by an RGB sensor. The RGB sensor has three photosensors provided with red (R), green (G), and blue (B) filters, respectively.

Since a current value i detected by the photosensors and the quantity of light are in direct proportion to each other, the quantity of light can be readily calculated from the measured current value i. In addition, the quantity of light and density D of the image are in the relationship shown below.

$$\text{Density } D = \log_{10}(I_0/I) \tag{1}$$

where $I_0$: intensity of incident light
$I$: intensity of reflected light

Accordingly, the density can be determined from the quantity of light radiating from a light source and the quantity of light calculated from the detected current value.

However, in cases where the density is measured as described above, an angle between the incident light radiated from the light source and the light reflected from the planar image recorded on a recording material, as well as an angle between the reflected light made incident upon the RGB sensor and a perpendicular direction (normal) to a detection surface of the RGB sensor are not necessarily constant but instead are dependent on the detection positions. As these angles vary, the detected value also varies, thereby making it impossible to effect the measurement in a stable manner. For this reason, an attempt has been made to minimize the aforementioned angular changes at each detection position through a mechanical means employing a tool such as a micro-tracer using a ball screw. With such an arrangement, however, a rise in the product cost is unavoidable.

SUMMARY OF THE INVENTION

Accordingly, an object of the present invention is to provide a method of measuring the reflected density of an image which is capable of correcting a quantity of reflected light from a planar image which is detected in correspondence with the aforementioned angular changes, and of obtaining an appropriate image density on the basis of the corrected quantity of light, thereby overcoming the above-described drawbacks of the conventional art.

To this end, in accordance with one aspect of the invention, there is provided a method of measuring a reflected density of an image for measuring the density of light in a visible region reflected from a planar image recorded on an image-recording material, comprising the steps of:

(a) placing in a predetermined plane a reference calibration plate whose reflection densities of certain wavelengths are already known and which does not exhibit spectral absorption in the predetermined invisible region. Then applying light in a predetermined invisible region to the reference calibration plate, and determining a quantity of light in the predetermined invisible region reflected from the reference calibration plate;

(b) disposing the recording material at the same position in the predetermined plane, and determining a quantity of light in the predetermined invisible region reflected from the recording material;

(c) determining a difference in the quantity of reflected light on the basis of a difference in spectral absorption between the reference calibration plate and the recording material in the predetermined invisible region;

(d) applying the light in the predetermined invisible region and the light in the visible region to the reference calibration plate, receiving the light reflected from the reference calibration plate, and determining a quantity of reflected light corresponding to the known density; and (e) at the time of setting the density of light in the visible region reflected from the planar image after applying the light in the predetermined invisible region and the light in the visible region to the recording material and after receiving the reflected light from the recording material, correcting the density of light, to be set, in the visible region reflected from the planar image in correspondence with a difference in the quantity of light between the light in the predetermined invisible region reflected from the reference calibration plate and the light in the predetermined invisible region reflected from the planar image as well as with the difference in the quantity of reflected light on the basis of the difference in the spectral absorption.

In accordance with this aspect of the invention, as described above, a reference calibration plate whose reflection densities for types of wavelength are already known and which does not exhibit spectral absorption in the predetermined invisible region is placed in a predetermined plane. Light in a predetermined invisible region is then applied to the reference calibration plate, and a quantity of light in the predetermined invisible region reflected from the reference calibration plate is measured.

Subsequently, the recording material is placed at this same position in the predetermined plane, a quantity of light in the predetermined invisible region reflected from the recording material is determined, and a difference in the quantity of reflected light is determined on the basis of a difference in spectral absorption between the reference calibration plate and the recording material in the predetermined invisible region.

Upon completion of the aforementioned measurements, the light in the predetermined invisible region and the light in the visible region are applied to the reference calibration plate, the light reflected from the reference calibration plate is received, and a quantity of reflected light corresponding to the known density is determined.

Then, the density of light in the visible region reflected from the planar image is obtained after the light in the predetermined invisible region and the light in the visible region are applied to the recording material and after the reflected light from the recording material is received.

The density of the planar image recorded on the image-recording material is determined on the basis of the quantity of reflected light thus obtained and the quantity of reflected light corresponding to the known density.

Here, at the time of measuring the quantity of light reflected from the reference calibration plate and from the planar image recorded on the image-recording material, there are cases where positional changes occur, including a change in the position of the object to be measured, a change in an angle between an incident beam of light radiating from the light source and the reflected beam of light, and a change in an angle between the reflected beam of light and a normal line to the receiving surface of a measuring device. The quantity of reflected light measured varies due to such changes.

In these cases, the difference in the quantity of light reflected from the reference calibration plate and that reflected from the recording material in the invisible region is a value greater than the difference in the quantity of reflected light based on the difference in the aforementioned spectral absorption. That is, this difference is one in which the difference in the quantity of reflected light attributable to positional changes is added to the difference in the quantity of reflected light based on the difference in the spectral absorption.

Accordingly, the density of light, to be determined, in the visible region reflected from the planar image is corrected in correspondence with a difference in the quantity of light between the light in the predetermined invisible region reflected from the reference calibration plate and the light in the predetermined invisible region reflected from the planar image as well as with the difference in the quantity of reflected light on the basis of the difference in the spectral absorption.

As a result, even if a positional change occurs, it is possible to constantly obtain an adequate reflected density.

As described above, in the method of measuring a reflected density of an image in accordance with this aspect of the invention, the quantity of reflected light in the predetermined invisible region detected changes due to angular changes of reflection or incidence of light radiating from the light source, reflected from the plane, and detected by sensors, or due to a positional change in the object to be measured. Accordingly, the method of the invention offers an outstanding advantage in that the quantity of reflected light detected in the visible region is corrected on the basis of these changes, and that an appropriate image density can be obtained on the basis of the quantity of light thus corrected.

In accordance with another aspect of the invention, there is provided a method of measuring a reflected density of an image for measuring the density of light in a visible region reflected from a planar image recorded on an image recording material not exhibiting spectral absorption in a predetermined invisible region, comprising the steps of:

(a) placing in the same plane as that of the planar image a reference calibration plate whose reflection densities for types of wavelength are already known and which does not exhibit spectral absorption in the predetermined invisible region;

(b) applying a beam of light including light in the visible region and light in the predetermined invisible region from a light source to the reference calibration plate, receiving reflected light from the reference calibration plate, and determining a quantity of light corresponding to the known density; and (c) at the time of setting the density of light in the visible region reflected from the planar image on the basis of the quantity of light in the visible region reflected from the planar image and on the basis of the quantity of light corresponding to the known density, correcting the density of light, to be set, in the visible region reflected from the planar image in correspondence with a difference in the quantity of light between the light in the predetermined invisible region reflected from the reference calibration plate and the light in the predetermined invisible region reflected from the planar image.

As described above, in accordance with this aspect of the present invention, the reference calibration plate whose density values for types of wavelength are already known is disposed within the same plane as that of the planar image recorded on the recording material, i.e., an object to be measured. Then, a beam of light is applied from the light source to the reference calibration plate, the light beam reflected from the reference calibration plate is received, and the quantity of light corresponding to the aforementioned known density is determined in advance. That is, the quantity of light thus determined is set as a unit density. Here, the quantity of light in the invisible region reflected from the reference calibration plate is also measured.

Upon completion of the aforementioned measurements, the light reflected from the planar image is received to determine its quantity of light. The density of the planar image is set on the basis of the quantity of light thus obtained and the quantity of light corresponding to the known density. Here, there are cases where the density obtained varies due to a change in the angle between the incident beam of light radiating from the light source and the reflected beam of light and due to a change in the angle between the reflected beam of light and the normal line to the receiving surface. In this aspect of the invention, the quantity of light in the invisible region reflected from the planar image is received, and the density of the reflected visible light, to be set, from the planar image is corrected in correspondence with the quantity of light in the invisible region reflected from the planar image and the quantity of light in the invisible region reflected from the reference calibration plate. As a result, it is possible to constantly obtain an appropriate density.

As described above, the method of measuring a reflected density of an image in accordance with this aspect of the invention offers an outstanding advantage in that the quantity of light detected in correspondence with a change in the angle of reflection or incidence of light radiating from the light source, reflected from the planar image, and detected by sensors is corrected, and it is possible to obtain an appropriate image density on the basis of the quantity of light thus corrected.

As the image-recording material and the reference calibration plate in the present invention, it is preferable to use those that do not exhibit spectral absorption in a predetermined invisible region. In this case, the difference in the quantity of reflected light in the invisible region based on the difference of spectral absorption in the invisible region becomes insubstantial, so that the correction of density based on the difference in the quantity of reflected light becomes unnecessary.

In addition, if the spectral absorption characteristics of the image-recording material and the reference calibration plate in the predetermined invisible region are substantially similar, the difference in the quantity of reflected light in the invisible region also becomes insubstantial, so that the correction of density based on the difference in the quantity of reflected light also becomes unnecessary.

In the embodiments shown below, cases are described in which the aforementioned difference in the quantity of reflected light is insubstantial, i.e., cases in which the recording material and the reference calibration plate exhibit substantially identical spectral absorption characteristics or do not exhibit spectral absorption in an invisible region.

DESCRIPTION OF THE PREFERRED EMBODIMENTS

Figure 1:
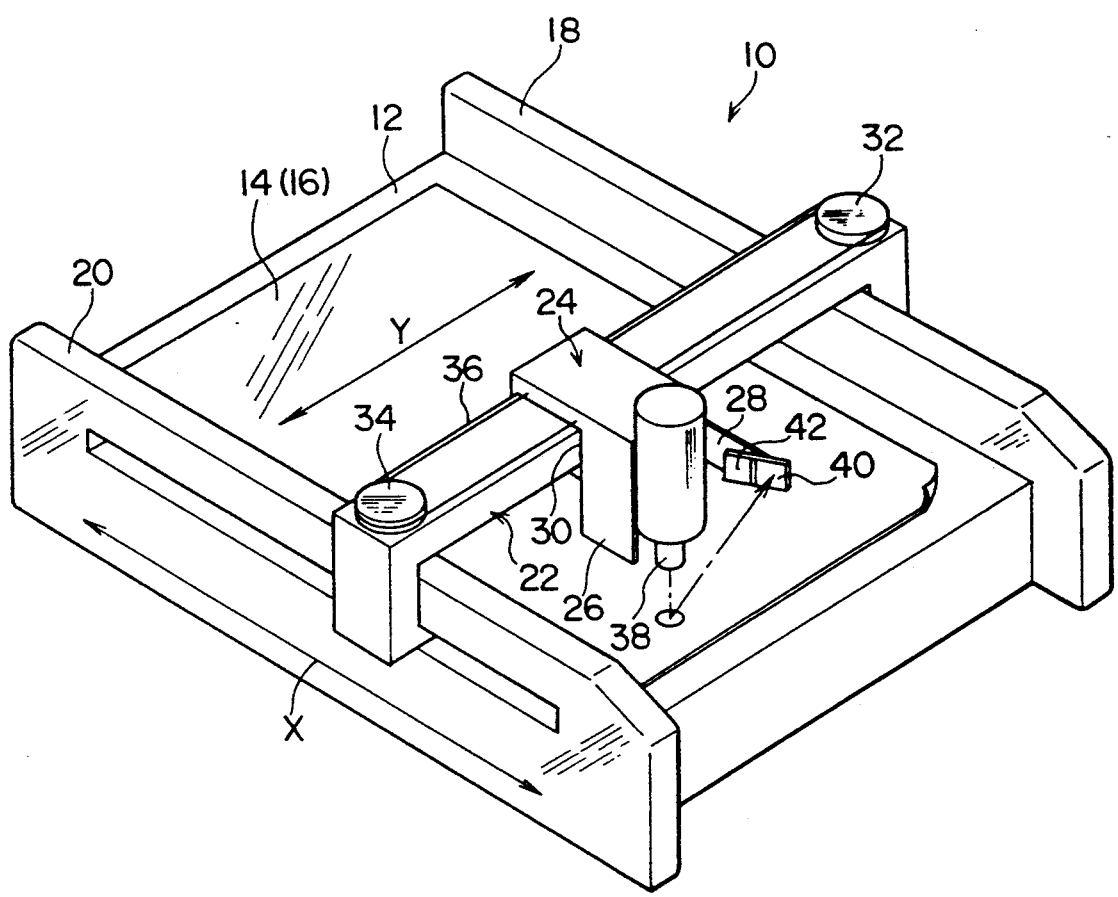
FIG. 1 is a perspective view of a density measuring apparatus in accordance with a first embodiment.
Figure 2:
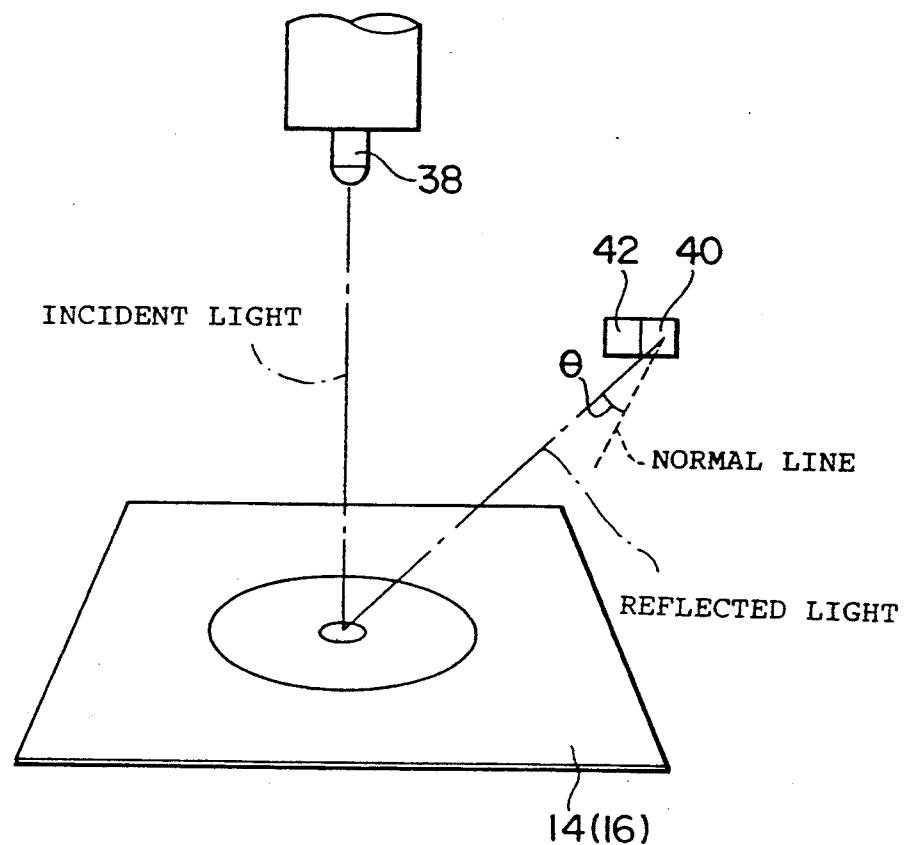
FIG. 2 is an enlarged view illustrating a moving block in accordance with the first embodiment and a measuring point.

FIG. 1 illustrates an apparatus 10 for measuring the density of an image in accordance with a first embodiment of the present invention. A table 12 is disposed in the center of the density measuring apparatus 10, and a recording material 14 with a planar image recorded thereon or a reference calibration plate 16 is adapted to be placed thereon. The reference calibration plate 16, whose densities of respective color components (R, G and B) are already known, is used as a reference plate employed prior to measuring the density of a planar image recorded on the recording material 14. Side walls 18, 20 are provided uprightly on transversely opposite sides of the table 12, an arm 22 extends between the two side walls 18, 20. The arm 22 is adapted to move by a driving force of an unillustrated driving mechanism in the longitudinal direction of the side walls 18, 20 (in the direction of arrow X in FIG. 1).

A moving block 24 having a leg 26 is provided on the arm 22. The leg 26 is provided with a bracket 28. The moving block 24 has a hole 30 in which the arm 22 is inserted. In addition, a portion of an endless belt 36 extended between a pair of pulleys 32, 34 which rotate by a driving force of an unillustrated driving means is secured to the moving block 24, whereby the moving block 24 is moved in the longitudinal direction of the arm 22 as the pulleys 32, 34 rotate (in the direction of arrow Y in FIG. 1). That is, the moving block 24 is moved over the table 12 in the directions of arrows X and Y in FIG. 1. It should be noted that these arrangements are similar to those of a conventional X-Y plotter, and should not be restricted to the above-described arrangements.

As shown in FIG. 1, a light source 38, an RGB sensor 40, and an infrared sensor 42 are attached to the moving block 24. The light source 38 is attached to the leg 26 of the moving block 24 and is arranged such that the direction of its irradiation is set to be substantially perpendicular to the table 12. A beam of light is radiated substantially perpendicular to the recording material 14 or the like placed on the table 12. The light beam thus radiated includes an entire visible region and infrared rays of light.

In addition, the RGB sensor 40 is constituted by three photosensors having the filters of red, green, and blue, respectively, and is attached to the bracket 28 of the moving block 24. A normal line to a detection surface of the RGB sensor 40 is oriented toward a point of irradiation (detection position) of the recording material 14 or the like with the light beam from the light source 38. Accordingly, the reflected light from the recording material 14, or the like, advances substantially perpendicularly to the detection surface of the RGB sensor 40. In addition, the infrared sensor 42 is also attached to the bracket 28 of the moving block 24 so as to be disposed within the same plane as that of the RGB sensor 40 and is adapted to detect the infrared light reflected from the recording material 14, or the like. Here, the recording material 14 in accordance with this embodiment is an image-receiving material onto which an image recorded on a heat-developable light-sensitive material has been transferred through heat development. Since the recording material 14 is one which does not absorb light having a wavelength of 700 nm or more, the recording material 14 reflects all the infrared light included in the light beam applied thereto from the light source.

Also, the aforementioned reference calibration plate 16 has the characteristic of totally reflecting the infrared light applied thereto. The quantity of infrared light reflected from the reference calibration plate 16 and the quantity of infrared light reflected from the recording material 14 assume identical values if the relative positions between the light source 38 and the infrared sensor 40 on the one hand, and the reflecting points on the other, agree with each other. Cases where these values differ are those in which a change has occurred in the angle formed between the light made incident from the light source 38 toward the table 12 and the light reflected from the recording material 14 or the like, and in the angle formed between the reflected light leading to the infrared sensor 42 and the detection surface of the infrared sensor 42. In this embodiment, the density obtained on the basis of the value detected by the RGB sensor is corrected in correspondence with the difference between the detection values of the quantities of infrared light.

That is, if it is assumed that an output of the infrared sensor 42 obtained when the reference calibration plate 16 is I, a density value based on the output of the RGB sensor 40 is D, the output of the infrared sensor 42 obtained by measuring the recording material 14 is I', a density value based on the output of the RGB sensor 40 is D', and an initial angle is $\theta_0$, the relationship of an angle of change $\Delta\theta$ is obtained from the following formula:

$$\frac{I'}{I} = \frac{\cos(\theta_0 + \Delta\theta)}{\cos\theta_0} \qquad (2)$$

Accordingly, if the measured value of the recording material 14 obtained by the RGB sensor 40 is corrected by this angle of change Δθ, it is possible to obtain an appropriate density value D".

$$D'' = D' - \log \frac{I'}{I} \quad (3)$$

A description will now be given of the operation of this embodiment.

First, the reference calibration plate 16 whose density values are already known is placed on the table 12 of the density measuring apparatus 10. Next, the arm 22 and the moving block 24 are moved in the directions of X and Y as shown in FIG. 1, respectively, so as to be disposed at predetermined positions over the reference calibration plate 16, and irradiation from the light source 38 commences. The light beam radiating from the light source 38 reaches the reference calibration plate 16 and is reflected thereby. The reflected light is received by the RGB sensor 40 and the infrared sensor 42. The density values of the respective color components of the reference calibration plate 16 and the detected outputs (current values) of the sensors are shown in the table below with the values rounded off to three decimal places.

|   | Density | Detected Output (mA) |
|---|---------|----------------------|
| R | 0.01    | 15                   |
| G | 0.01    | 17                   |
| B | 0.01    | 28                   |
| Infrared light | — | 60 |

Upon completing the measurement of the reference calibration plate 16, the recording material 14 onto which an image, i.e., an object to be measured, has been recorded in advance is placed on the table 12 instead of the reference calibration plate 16. As a result, the reference calibration plate 16 and the recording material 14 are placed in the same plane. A single measurement point or a plurality of measurement points may be selected on the recording material 14. After the arm 22 and the moving block 24 are moved, and the positioning with respect to the initial measurement point is completed, the light beam reflected from the recording material 14 is received and measured by the RGB sensor 40 and the infrared sensor 42 in the same procedure as that for measuring the reference calibration plate 16. It should be assumed that in this example the detected output value for R is 5 mA, that for G is 8 mA, that for B is 12 mA, and that for infrared light is 65 mA.

On the basis of the foregoing results, the density of each color component after being rounded off to three decimal places becomes $R = 0.01\text{-log }(5/15) = 0.49$ $G = 0.01\text{-log }(8/17) = 0.34$ $B = 0.01\text{-log }(12/28) = 0.38$ Here, in cases where the angle between the incident light from the light source 38 and the reflected light as well as the angle between the reflected light and the receiving surface of the infrared sensor 42 agree with each other at the time of measurement of the reference calibration plate 16 and at the time of measurement of the recording material 14, the detected output values obtained by the infrared sensor 42 become identical. However, the detected output values in this example are different, as shown above. Therefore, it follows that the detected angles have varied, and the calculated density values are not true values. Accordingly, the aforementioned density values are corrected on the basis of Formula (3) (I/I'=60/65). Incidentally, the detected outputs obtained when the recording material 14 is measured, pre-correction density values, and post-correction values (all rounded off to two decimal places) are shown in the table below.

|   | Detected Output | Pre-correction Density | Post-correction Density |
|---|-----------------|------------------------|-------------------------|
| R | 5               | 0.49                   | 0.52                    |
| G | 8               | 0.34                   | 0.37                    |
| B | 12              | 0.38                   | 0.41                    |
| Infrared light | 65 | — | — |

Thus, in this embodiment, variations in density values caused by the angular changes of the light source 38, the RGB sensor 40, and the infrared sensor 42 can be corrected on the basis of the detected quantity of the infrared light totally reflected from the reference calibration plate 16 and the recording material 14. By this method it is possible to consistently obtain an accurate density measurement.

A description will now be given of a second embodiment of the present invention.

In the foregoing first embodiment, the detection positions of the RGB sensor 40 and the infrared sensor 42 differ, though slightly, and the orientation of the detection surfaces of the sensors is set with a high degree of positioning accuracy. In the second embodiment, however, the positioning of the detection surfaces of the sensors is facilitated. A detailed description of the second embodiment will be given hereafter. Like components as those of the first embodiment are denoted by the same reference numerals and a description of their configurations will be omitted.

Figure 3:
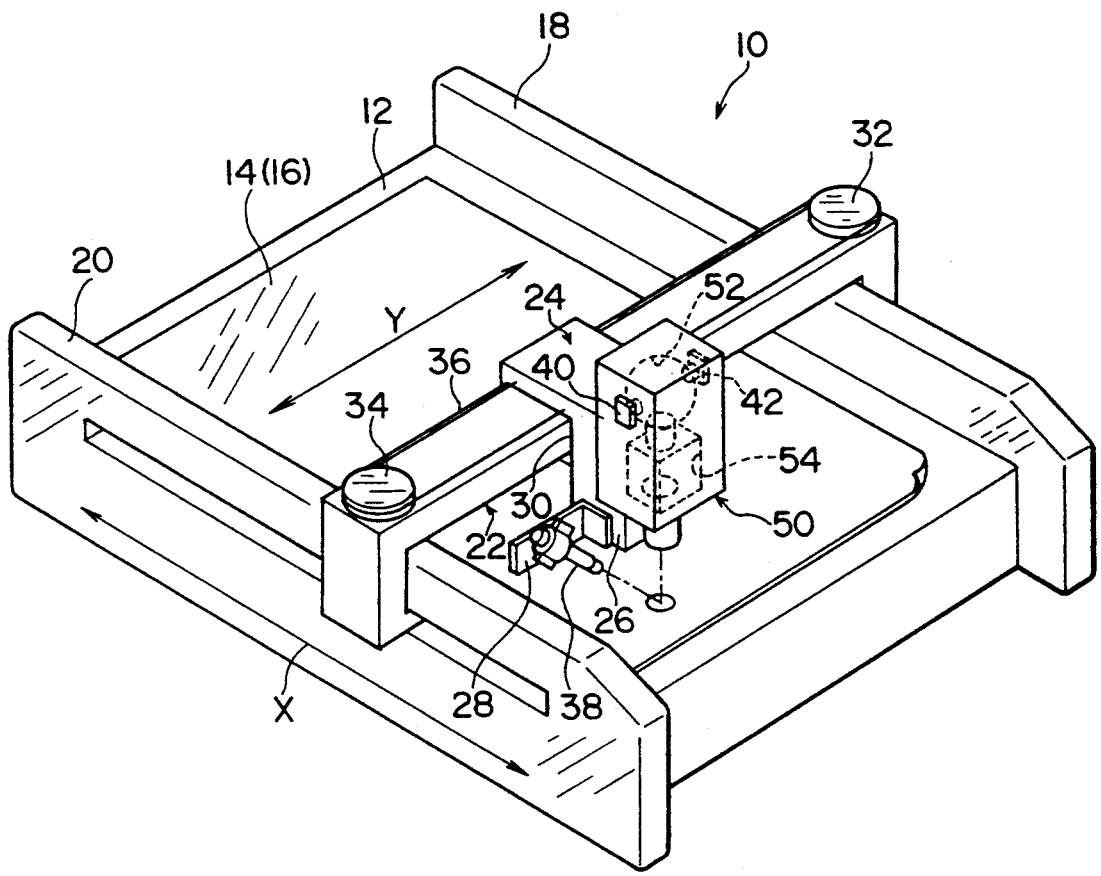
FIG. 3 is a perspective view of a density measuring apparatus in accordance with a second embodiment.
Figure 4:
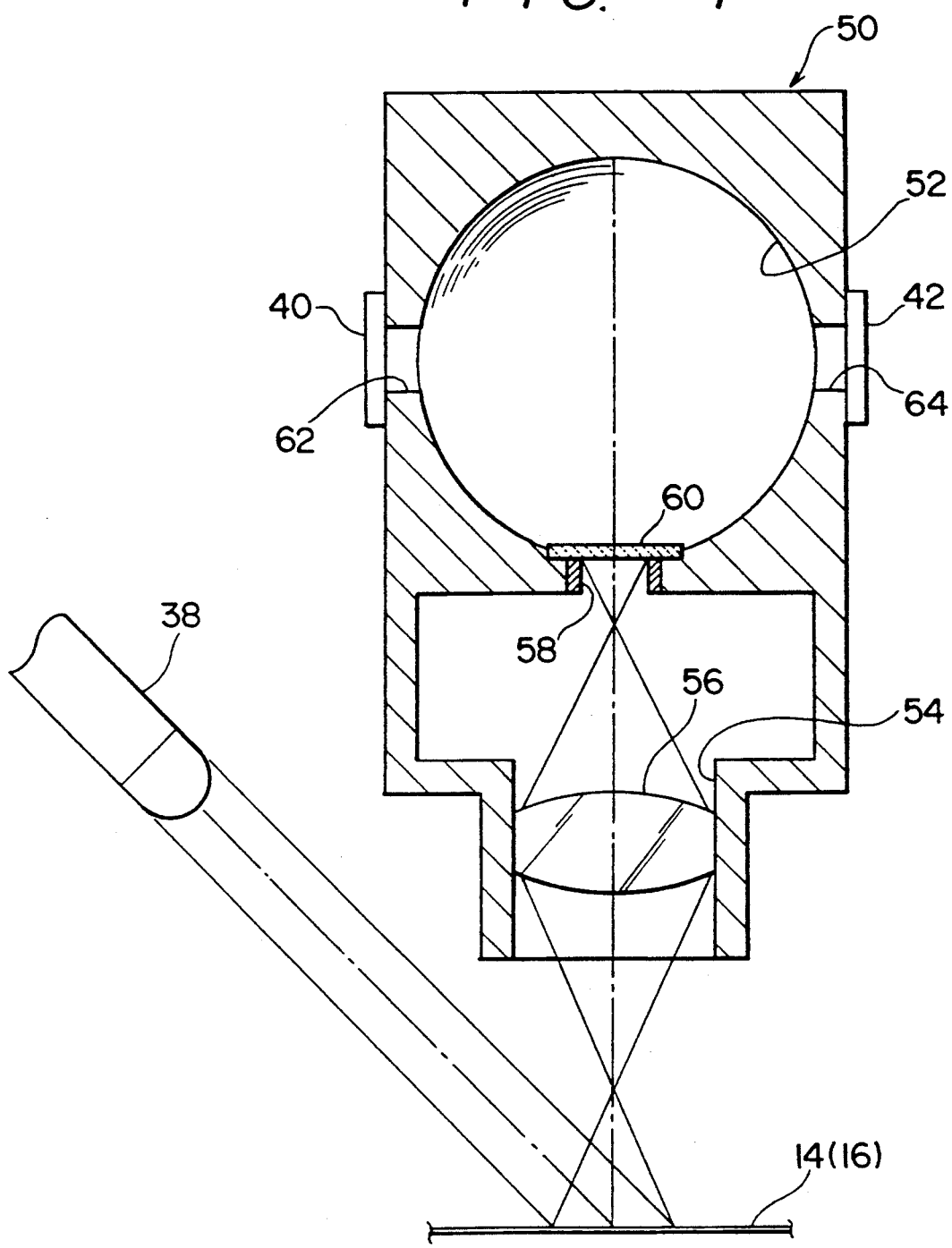
FIG. 4 is an enlarged view illustrating a moving block in accordance with the second embodiment and a measuring point.

As shown in FIGS. 3 and 4, the moving block 24 is provided with a detecting block 50 having a light source 38, a RGB sensor 40, and an infrared sensor 42. The light source 38 is attached to a bracket 28 of the moving block 24, and its angle of radiation is set to substantially 45 degrees with respect to the table 12 so that a light beam is applied diagonally to the recording material 14, or the like, placed on the table 12. In addition, the light beam thus applied includes an entire visible region and infrared rays of light.

In addition, the detecting block 50 is attached to the leg 26 of the moving block 24. A hollow portion 52 having a spherical inner peripheral surface is provided inside the detecting block 50. The inner peripheral surface of the hollow portion 52 is formed into a mirror surface. A guide passage 54 for guiding the reflected light beam into the hollow portion 52 is formed below the hollow portion 52 as viewed in FIG. 4. A portion of the guide passage 54 in the vicinity of an inlet thereof is formed into a small-diameter portion, and a lens 56 is provided therein. In addition, an aperture 58 is provided at an outlet of the guide passage 54, i.e., a boundary portion between the guide passage 54 and the hollow portion 52 so as to prevent an undesired light beam from entering the hollow portion 52. A diffusion plate 60 is fitted on the aperture 58 so as to diffuse the light beam reaching the hollow portion 52.

A pair of through-holes 62, 64 are provided in the inner peripheral surface of the hollow portion 52 in such a manner as to face each other. The RGB sensor 40 and the infrared sensor 42 are respectively fitted on the openings of the through-holes 62, 64 in a corresponding manner. As a result, the light beam entering the hollow portion 52 passes through the through-holes 62, 64, and the quantities of light are detected by the RGB sensor 40 and the infrared sensor 42. Here, the RGB sensor 40 and the infrared sensor 42 are arranged such that optical path lengths leading to the sensors are identical and detection is carried out at effectively the same optical position. That is, since the light beam reaching the hollow portion 52 from the diffusion plate 60 is reflected by the mirror surface which is formed into a spherical configuration on the entire periphery thereof, optical path lengths from any position on the inner peripheral surface become identical.

A description will now be given of the operation of the second embodiment.

If radiation of a light beam from the light source 38 is commenced to a predetermined position on the reference calibration plate 16 placed on the table 12, the light beam reflected by the reference calibration plate 16 is guided by the guide passage 54 and reaches the hollow portion 52 via the lens 56, the aperture 58, and the diffusion plate 60. The reflected light which has reached the hollow portion 52 is reflected by the inner peripheral mirror surface, is transmitted through the through-holes 62, 64, and is received by the RGB sensor 40 and the infrared sensor 42.

Upon completion of the measurement of the reference calibration plate 16, the recording material 14 with an image recorded thereon, i.e., an object to be measured, is placed on the table 12 in place of the reference calibration plate 16. As a result, the reference calibration plate 16 and the recording material 14 are placed in the same plane. After the arm 22 and the moving block 24 are moved, and the position corresponding to the initial measurement point is reached, the reflected light from the recording material 14 is received and measured by the RGB sensor 40 and the infrared sensor 42 in the same procedure as that for measuring the reference calibration plate 16.

Since the correction of the measured results is similar to that for the first embodiment, a description thereof will be omitted.

Thus, in accordance with the second embodiment, by using the hollow portion 52 having the spherical inner peripheral surface, the positions for detection by the RGB sensor 40 and the infrared sensor 42 become apparently the same, so that it is possible to set the RGB sensor 40 and the infrared sensor 42 with a higher degree of positioning accuracy than in the case of the first embodiment.

In addition, in this second embodiment, in addition to the correction of variations of the quantities of detected light attributable to the changes in the position of incidence of the light upon the light-receiving sensor, the variation of the quantity of light of the light source is corrected. Namely, if it is assumed that an output current of the RGB sensor 40 and an output current of the infrared sensor 42 with respect to the reference calibration plate 16 are $I_0$ and $I$, respectively, while an output current of the RGB sensor 40 and an output current of the infrared sensor 42 with respect to the recording material 14 are $I_n'$ and $I'$, respectively, then we have $$I_n' = I_0 \times s \times u \times t \qquad (4)$$

$$I' = I \times s \times u \qquad (5)$$

where
s: rate of variation of reflected light attributable to a positional change based on a height h and an angle $\theta$
t: rate of variation of reflected light attributable to absorption by a coloring material which has been colored on the basis of an amount of coloring n
u: rate of variation of reflected light attributable to variations in the quantity of light issuing from the light source Here, the rate of variation of reflected light attributable to variations in the quantity of light issuing from the light source as well as the rate of variation of reflected light attributable to a positional change based on a height h and an angle $\theta$ are canceled by obtaining a reference current $I_n$ for calculating the density value by correcting the output current $I_n'$ of the RGB sensor 40 with respect to the recording material 14 by using the rate of variation $I/I'$ of the output current of the infrared sensor 42 with respect to both the reference calibration plate 16 and the recording material 14. That is, $$I_n = I_n' \times I/I' = I_0 \times t \qquad (6)$$

Figure 5:
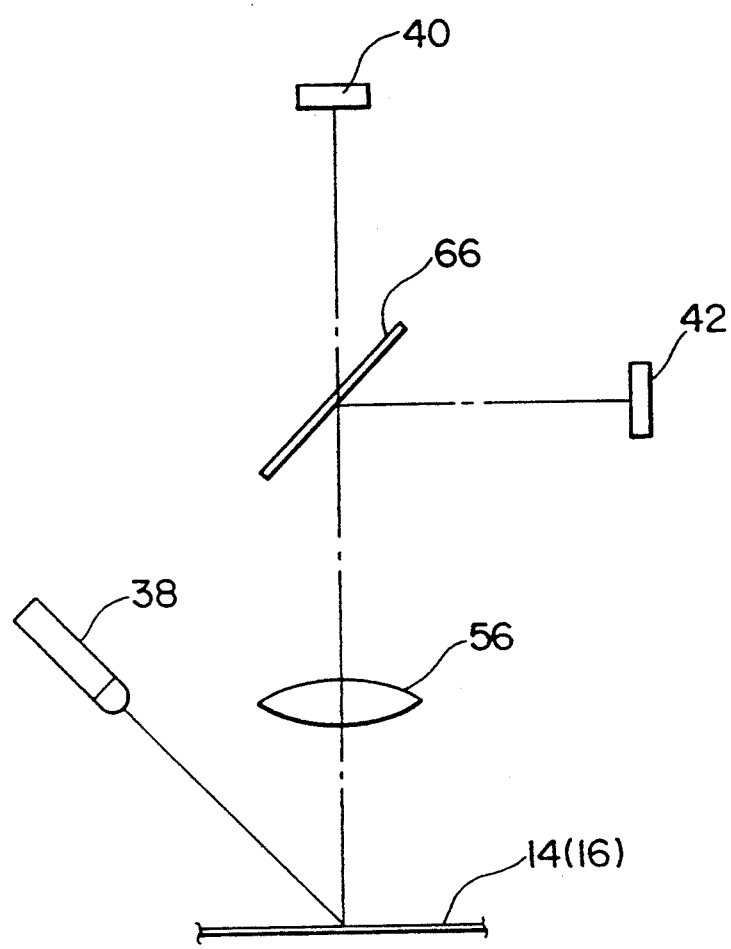
FIG. 5 is a schematic diagram of a density measuring apparatus using a half mirror.

It should be noted that although in the second embodiment the detection block 50 provided with the hollow portion 52 having the peripheral surface on the inner periphery thereof is used so as to set the positions of the RGB sensor 40 and the infrared sensor 42 such as to be apparently the same, an arrangement may be alternatively provided such that by using a half mirror 66, as shown in FIG. 5, the RGB sensor 40 is disposed on the transmission side of the half mirror 66 and the infrared sensor 42 is disposed on the reflection side thereof.

In addition, although in the first and second embodiments the current value is set as the detected output, a digital value proportional to a voltage value, a current value, or a voltage value may be used. Furthermore, although in the embodiments infrared light is used as the light in an invisible region, ultraviolet light or the like in another invisible region may be used.

What is claimed is:

1. A method of measuring a reflected density of an image for measuring the density of light in a visible region reflected from a planar image recorded on an image-recording material not exhibiting spectral absorption in a known invisible region, comprising the steps of:

placing in a predetermined plane a reference calibration plate whose reflection densities for known wavelengths are already known and which does not exhibit spectral absorption in said known invisible region;

applying a beam of light including light in the visible region and light in said known invisible region from a light source to said reference calibration plate, receiving reflected light from said reference calibration plate, and determining a first quantity of invisible reflected light and a second quantity of visible reflected light corresponding to said known density; and removing said calibration plate and disposing said image recording material in said predetermined plane, applying said beam of light including light in the visible region and light in said known invisible wavelength region from said light source to said image recording material, receiving reflected light from said image recording material, and determining a third quantity of invisible light reflected from said planar image and a fourth quantity of visible light reflected from said planar image; and correcting the density of light, to be determined, in the visible region reflected from said planar image in correspondence with a difference in said first and third quantities.

2. A method of measuring a reflected density of an image according to claim 1, wherein the light in said predetermined invisible region is constituted by one of an infrared light and an ultraviolet light.

3. A method of measuring a reflected density of an image according to claim 1, wherein the quantity of light is determined on the basis of one of a current value and a voltage value of a sensor for receiving the reflected light as well as a digital value proportional to one of said values.

4. A method of measuring a reflected density of an image for measuring the density of light in a visible region reflected from a planar image recorded on an image-recording material not exhibiting spectral absorption in a predetermined invisible region, comprising the steps of:

placing in a predetermined position a reference calibration plate whose reflection densities for types of wavelength are already known and which does not exhibit spectral absorption in said predetermined invisible region;

applying a beam of light including light in the visible region and light in said predetermined invisible region from a light source to said reference calibration plate, and determining a first quantity of light in the visible region reflected from said reference calibration plate and a second quantity of light in said predetermined invisible region reflected from said reference calibration plate, respectively;

removing said calibration plate and placing said recording material in said predetermined position in place of said reference calibration plate;

applying said beam of light including said light in the visible region and said light in said predetermined invisible region from said light source to the planar image of said recording material, and determining a third quantity of light in the visible region reflected from the planar image and a fourth quantity of light in said predetermined invisible region reflected from the planar image;

determining a density of light in the visible region reflected from the planar image on the basis of a relationship between the known density and said first quantity and said third quantity; and correcting said density of light in the visible region reflected from the planar image in correspondence with a difference between said second quantity and said fourth quantity.

5. A method of measuring a reflected density of an image according to claim 4, wherein said first quantity and said third quantity of reflected light in the visible region is measured by a first sensor, and said second quantity and said fourth quantity of reflected light in the invisible region is measured by a second sensor.

6. A method of measuring a reflected density of an image according to claim 5, wherein an optical path length of the reflected light in the visible region to said first sensor and an optical path length of the reflected light in said predetermined invisible region are substantially the same.

7. A method of measuring a reflected density of an image according to claim 5, wherein the quantities of light measured by said first and second sensors are transduced into current values.

8. A method of measuring a reflected density of an image according to claim 4, wherein the light in the predetermined invisible region is constituted by infrared light.

9. A method of measuring a reflected density of an image for measuring the density of light in a visible region reflected from a planar image recorded on an image-recording material not exhibiting spectral absorption in a predetermined invisible region, comprising the steps of:

placing in a predetermined position a reference calibration plate whose reflection densities for predetermined wavelengths are already known and which does not exhibit spectral absorption in said predetermined invisible region;

applying a beam of light including light in the visible region and light in said predetermined invisible region from a light source to said reference calibration plate, determining a first measurement value by measuring a first quantity of light in the visible region in the light reflected from said reference calibration plate, and determining a second measurement value by measuring a second quantity of light in the predetermined invisible region in the light reflected from said reference calibration plate;

removing said calibration plate and placing said recording material in said predetermined position in place of said reference calibration plate;

applying said beam of light including said light in the visible region and said light in said predetermined invisible region from said light source to said recording material, determining a third measurement value by measuring a third quantity of light in the visible region in the light reflected from the planar image of said recording material, and determining a fourth measurement value by measuring a fourth quantity of light in the predetermined invisible region in the light reflected from said recording material, respectively;

determining a density of light in the visible region reflected from the planar image on the basis of a relationship between said known density and the first measurement value and on the basis of the third measurement value;

correcting the density of light in the visible region reflected from the planar image in correspondence with a difference between the second measurement value and the fourth measurement value.

10. A method of measuring a reflected density of an image according to claim 9, wherein the first, second, third, and fourth measurement values are measured as current values.

11. A method of measuring a reflected density of an image according to claim 9, wherein the light in the predetermined invisible region is constituted by infrared light.

* * * * *